United States Patent
Rutherford et al.

(10) Patent No.: US 7,487,563 B2
(45) Date of Patent: Feb. 10, 2009

(54) DEVICE FOR SUPPORTING AT LEAST ONE ARM OF AN OPERATING PERSON DURING A SURGICAL OR MEDICAL OPERATION

(75) Inventors: Ian Rutherford, Dundee (GB); Leslie Kelly, Cupar (GB); Stuart Brown, St. Andrews (GB); Timothy Graham Frank, Wormit Newport-On-Tay Fife (GB); Alfred Cuschieri, St. Andrews Fife (GB)

(73) Assignee: University of Dundee (GB)

( * ) Notice: Subject to any disclaimer, the term of this patent is extended or adjusted under 35 U.S.C. 154(b) by 403 days.

(21) Appl. No.: 11/297,240

(22) Filed: Dec. 8, 2005

(65) Prior Publication Data
US 2006/0226319 A1 Oct. 12, 2006

(30) Foreign Application Priority Data
Dec. 9, 2004 (EP) .................................. 04029165

(51) Int. Cl.
*A61G 13/10* (2006.01)
*A61G 13/12* (2006.01)
(52) U.S. Cl. .................... 5/623; 5/646; 5/657; 248/118
(58) Field of Classification Search .................... 5/623, 5/646, 647, 503.1, 507, 652, 657; 248/278.1, 248/118
See application file for complete search history.

(56) References Cited

U.S. PATENT DOCUMENTS

| | | | | |
|---|---|---|---|---|
| 3,124,328 A | * | 3/1964 | Kortsch | 248/118 |
| 4,390,011 A | * | 6/1983 | Evans | 5/507.1 |
| 5,281,001 A | * | 1/1994 | Bergsten et al. | 297/411.24 |
| 6,102,344 A | | 8/2000 | Kasvin et al. | |
| 6,271,828 B1 | | 8/2001 | Rosenberg et al. | |
| 6,704,959 B2 | * | 3/2004 | Schuerch | 5/648 |
| 6,925,668 B2 | * | 8/2005 | Cuschieri et al. | 5/623 |
| 2003/0028967 A1 | | 2/2003 | Schuerch | |

FOREIGN PATENT DOCUMENTS

DE 195 04 838 2/1995
EP 0 868 885 10/1998

* cited by examiner

*Primary Examiner*—Michael Trettel
(74) *Attorney, Agent, or Firm*—St. Onge Steward Johnston & Reens LLC

(57) ABSTRACT

A device for supporting at least one arm of an operating person during a surgical or medical operation comprises at least one supporting element for supporting the at least one arm of the operating person, the supporting element being arranged at a carrying structure for carrying the at least one supporting element. The carrying structure is configured such that the at least one supporting element can be lowered or raised for adjusting the height of the operating person's arm. The carrying structure comprises a control system which comprises a hydraulic circuit for lowering or raising the at least one supporting element.

7 Claims, 2 Drawing Sheets

DEVICE FOR SUPPORTING AT LEAST ONE ARM OF AN OPERATING PERSON DURING A SURGICAL OR MEDICAL OPERATION

CROSS REFERENCE TO RELATED APPLICATION

The present application claims priority of European patent application No. 04 029 165.0 filed on Dec. 9, 2004.

BACKGROUND OF THE INVENTION

The invention relates to a device for supporting at least one arm of an operating person during a surgical or medical operation.

A device of the kind mentioned at the outset, which can also be designated as an arm rest, is used as a support of the surgeon's or the surgical assistant's arm during an operation in order to increase steadiness of movement and reduce fatigue. Taking into consideration that a surgical operation can take up several hours and the surgical personnel carries out such an operation in a standing position, an arm rest of the afore-mentioned kind will be effective in avoiding a loss of preciseness of the manipulations carried out by the operating person.

The supporting device comprises at least one supporting element for supporting the at least one arm of, for example, the surgeon. The supporting element is arranged at the carrying structure for carrying the at least one supporting element, wherein the carrying structure should be adapted to be mounted on a side of the operating table or in front of a surgical stool. However, the carrying structure of the device according to the invention can also be configured as a self-standing structure which can stand on the floor of the operating room beside the operating table.

In particular, an arm rest is very useful in complex laparoscopic surgery which requires precise movements, and usually long execution times of the operating person. Discomfort in the shoulders, back and neck is an established complaint amongst laparoscopic surgeons and is related to the unnatural postures adopted during laparoscopic intervention. Discomfort, and the associated fatigue, is a contributory factor in the execution of errors. A supporting arm rest provides the benefit of avoiding such disadvantages.

A device known from DE 195 04 838 A1 is a supporting device integrated into an operating stool which can also be integrated in the operating table. The operating stool comprises an adjustable arm rest supporting the arms or hands of the surgeon leading over the operating area.

However, in that document it is not disclosed how to adjust the height of the supporting element and, accordingly, the surgeon's or surgical assistance's arm or hand.

SUMMARY OF THE INVENTION

Therefore, it is an object of the present invention to provide a device of the kind mentioned at the outset which allows an easy adjustment of the height of the at least one supporting element while ensuring that the supporting element is safely held in the adjusted height position.

According to an aspect of the invention, a device for supporting at least one arm of an operating person during a surgical or medical operation is provided, comprising at least one supporting element for supporting the at least one arm of the operating person, a carrying structure for carrying the supporting element at which the supporting element is arranged, the carrying structure being configured such that the at least one supporting element can be lowered or raised for adjusting a height of the operating person's arm, and the carrying structure having a control system which comprises a hydraulic circuit for lowering or raising the at least one supporting element.

The device according to the invention provides an easily-to-be-operated mechanism for lowering or raising the at least one supporting element by virtue of the hydraulically controlled actuating mechanism for the at least one supporting element. The hydraulic control system has the advantage that the locking of the adjusted height of the supporting element can be achieved without further locking mechanisms, because of the incompressibility of hydraulic media which can be used in the hydraulic circuit. Thus, the supporting device according to the invention can be configured in a structurally very simple manner while allowing an easy adjusting of the height of the at least one supporting element.

In a preferred embodiment, the hydraulic circuit comprises a hydraulic ram operatively connected to the supporting element, wherein the hydraulic circuit comprises at least a control valve which can be closed and opened for controlling the flow of fluid between a first chamber and a second chamber of the hydraulic ram.

By providing a hydraulic circuit which comprises a hydraulic ram and a control valve for controlling the flow of fluid between two chambers of the hydraulic ram, a structurally very simple hydraulic circuit is obtained which can fulfil the above-mentioned functions of a safe control for lowering or raising the at least one supporting element.

In this context, it is preferred, if the supporting element can be lowered only when the control valve is open.

The advantage of this measure is that the control valve in its closed state prevents the hydraulic fluid to flow between the chambers thereby providing a simple locking mechanism in order to lock the height of the supporting element which has been adjusted by the operating person. For lowering the supporting element, the control valve just has to be opened thus allowing the hydraulic fluid to flow from the first chamber into the second chamber. It can also be envisaged that raising the supporting element is only possible, when the control valve is opened, but it could also be envisaged that raising the supporting element can be possible in the closed state of the control valve.

In order to provide an easy-to-be-maneuvered operating mechanism for the control valve, the control valve is preferably operatively connected to an operating element for closing or opening the control valve.

Such an operating element can be provided at the control valve itself, or it can be located remote from the control valve so that the control valve can be positioned at a location where it does not form an impediment to the use of the device, while the operating element can be positioned in proximity of the supporting element for comfortable operation.

Further, it is preferred if the control valve is electrically actuable, and the operating element is an electrical switch, or if the control valve is mechanically actuable, and the operating element is a push button.

In the latter embodiment, the advantage of a hydraulic circuit which does not require a power supply for actuating the control valve is achieved.

In a further preferred embodiment, the control valve and/or the operating element is biased such the control valve is closed when the operating element is not actuated.

The advantage here is that the control valve normally is in its closed state thus ensuring that the adjusted height of the supporting element is maintained when the operating person's arm leans on the supporting element and the operating person carries out a surgical operation.

Further, it is preferred, if the biasing load is adjustable.

The advantage here is that the force required to operate the operating element and thereby to actuate the control valve can be adjusted according to the operating person's needs.

In a further preferred embodiment, the at least one operating element is arranged on or near the supporting element.

The advantage of this measure is that the operating element can be operated by the user of the device without the arm being removed from the supporting element thus enhancing the comfort of the supporting device in terms of its handling.

In a further preferred embodiment, the operating element is arranged on the supporting element in a position above a portion of the supporting element on which the operating person's arm rests in use of the device.

The arrangement of the operating element in this way is in particular advantageous because the operating element can be operated by the user by simply lifting the arm resting on the supporting element against the operating element thus further enhancing the comfort in adjusting the height of the supporting element.

In a further preferred embodiment, the flow resistance of a hydraulic medium of the hydraulic circuit is adjustable.

The flow resistance influences the speed of downward or upward movement of the supporting element. By adjusting the flow resistance of the hydraulic medium of the hydraulic circuit it is possible to adjust a desired speed for adjusting the height of the supporting element according to the user's needs.

Further features and advantages will be apparent from the following description and the accompanying drawings.

It is to be understood that the features mentioned before and those features yet to be explained hereinafter are not only applicable in the given combination, but also in other combinations or in isolation without departing from the scope of the present invention.

BRIEF DESCRIPTION OF THE DRAWINGS

Exemplary embodiments of the invention are shown in the drawings and will be explained below with reference to the drawings. In the drawings.

DETAILED DESCRIPTION OF PREFERRED EMBODIMENTS

Figure 1:
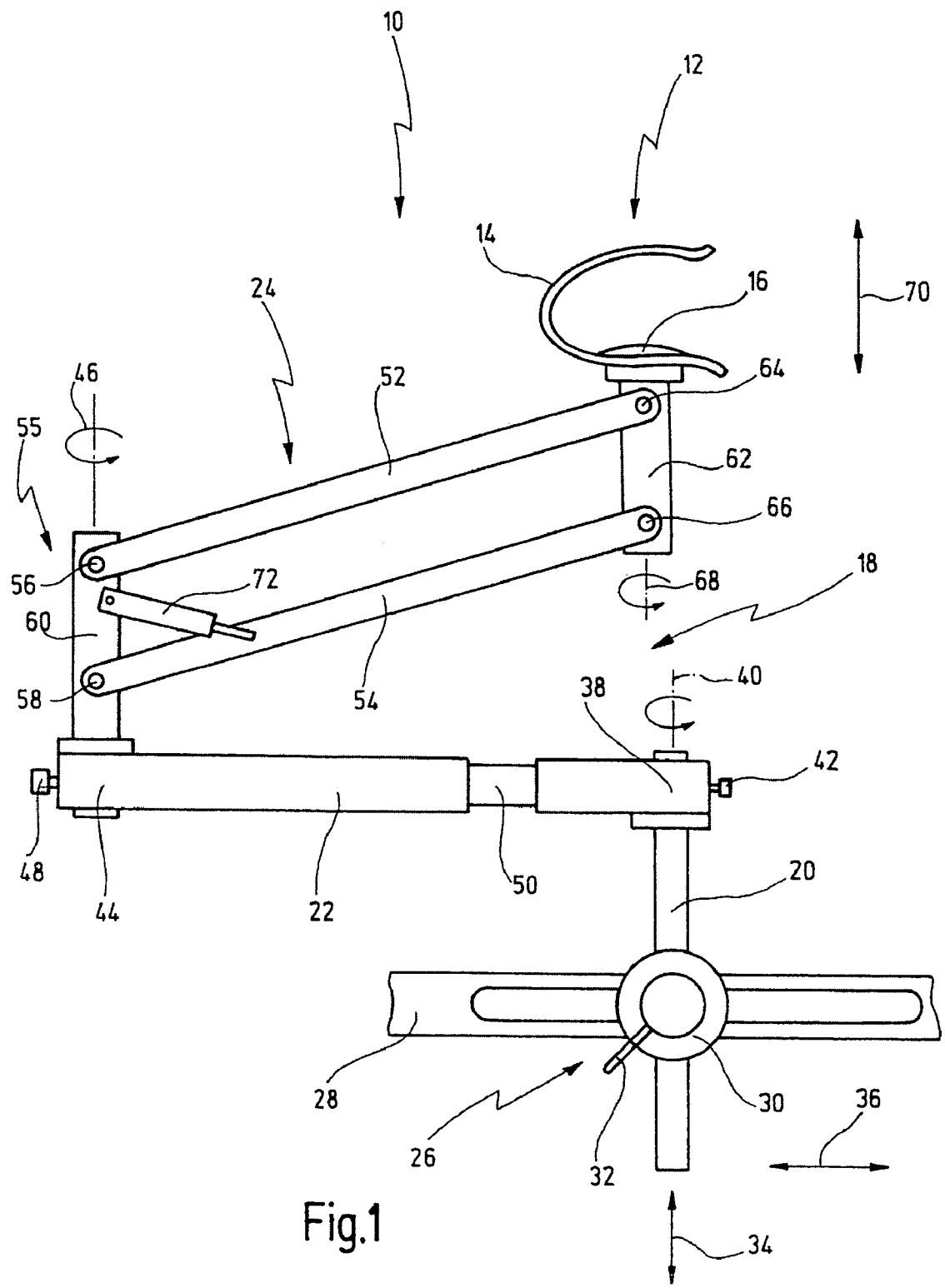
FIG. 1 schematically shows a device for supporting at least one arm of an operating person in a side view showing the general design of the device.

FIG. 1 shows a device labeled in its entirety with reference numeral 10 for supporting at least one arm of an operating person (not shown) during a surgical or medical operation.

The device 10 can be used for all surgical disciplines, but is in particular useful for laparoscopic or other endoscopic procedures.

The device 10 comprises at least one supporting element 12 for supporting at least one arm of, for example, the surgeon or surgical assistant.

The supporting element 12 comprises a C-shaped element 14 in which the operating person's forearm in the region between the wrist and the elbow can be accommodated. A contact pad 16 of the supporting element 12 provides for a better comfort to the operating person.

The supporting element 12 is arranged at a carrying structure 18 for carrying the at least one supporting element 12.

The carrying structure 18 comprises a first carrying arm 20 extending vertically or substantially vertically, a second carrying arm 22 connected to the first carrying arm 20 and extending horizontally or substantially horizontally, and a third carrying arm 24 connected to the second carrying arm 22. The supporting element 12 is connected to the third carrying arm 24.

The third carrying arm 24 will be described in more detail below.

The device 10 further comprises a mounting portion 26 for mounting the device 10 to an underlying support structure 28 which is, for example, an operating table or operating stool. The mounting portion 26 comprises an adjustable mounting bracket 30 receiving the first carrying arm 20. The mounting bracket 30 comprises a bracket lock 32 for locking the carrying arm 20 in a desired position to the underlying support structure 28. After releasing the bracket lock 32, the carrying arm 20 can be adjusted in height according to a double arrow 34 for a rough height adjusting of the entire device 10. Further, after releasing the bracket lock 32, the carrying arm 20 can also be displaced in horizontal direction according to a double arrow 36. Furthermore, after releasing the bracket lock 32 it is also possible to lift up the first carrying arm 20 and thereby the entire device 10 out of the mounting bracket 30 for removing the device 10 from the underlying structure.

The first carrying arm 20 is connected with the second carrying arm 22 via a joint 38 so that the carrying arm 22 can be rotated clockwise or counter-clockwise about a vertical or substantially vertical rotation axis 40. The rotation of the second carrying arm 22 is preferably possible over a full angle of 360°.

A friction adjuster 42 is provided in order to adjust the friction opposing the rotary movement of the second carrying arm 22 about the rotation axis 40.

The third carrying arm 24 is connected with the second carrying arm 22 via a further joint 44 allowing rotation of the third carrying arm 24 about a further vertical or substantially vertical rotation axis 46 in clockwise or counter-clockwise direction, and preferably over a full angle of 360°. A further friction adjuster 48 is provided in order to adjust the friction of the joint 44 so that the force necessary to move the first carrying arm 24 about the rotation axis 46 can be adjusted to the operating person's needs.

The second carrying arm 22 is optionally provided with a length adjustment, for example by configuring the second carrying arm 22 as a telescopic arm as indicated by reference numeral 50.

The third carrying arm 24 is configured, according to the embodiment in FIG. 1, as a parallelogram, which comprises a first parallelogram arm 52 and a second parallelogram arm 54 which are spaced from one another in vertical direction. The first and second parallelogram arms 52 and 54 are preferably configured as pairs of parallelogram arms in each case, i.e. there are further parallelogram arms arranged parallel to the parallelogram arms 52 and 54 in a plane behind the plane of the drawing in FIG. 1.

The third carrying arm 24 as a whole is pivotable about an at least approximately horizontal pivot axis 55, and in the configuration of the third carrying arm 24 as a parallelogram, there is a pivot axis 56 for the parallelogram arm 52 and a pivot axis 58 for the parallelogram arm 54.

The pivot axes 56 and 58 are provided at a vertical post 60 connected to the second carrying arm 22.

The supporting element 12 is connected to the third carrying arm 24, i.e. to the parallelogram arms 52 and 54 via a further vertical post 62 to which the parallelogram arms 52 and 54 are also pivotably connected via pivot axes 64 and 66. The supporting element 12 is rotatably connected to the post 62 so that the supporting element 12 can be rotated about a vertical or substantially vertical rotation axis 68 relative to the carrying structure 18.

By pivoting the third carrying arm 24 about the pivot axis 55, i.e. more exactly about the pivot axes 56 and 58, the supporting element 12 which is carried by the third carrying arm 24, can be lowered or raised according to a double arrow 70.

Optionally, a bias force element 72 can be provided which biases the third carrying arm 24 in the upward direction or in the downward direction, if desired.

Figures 2, 3:
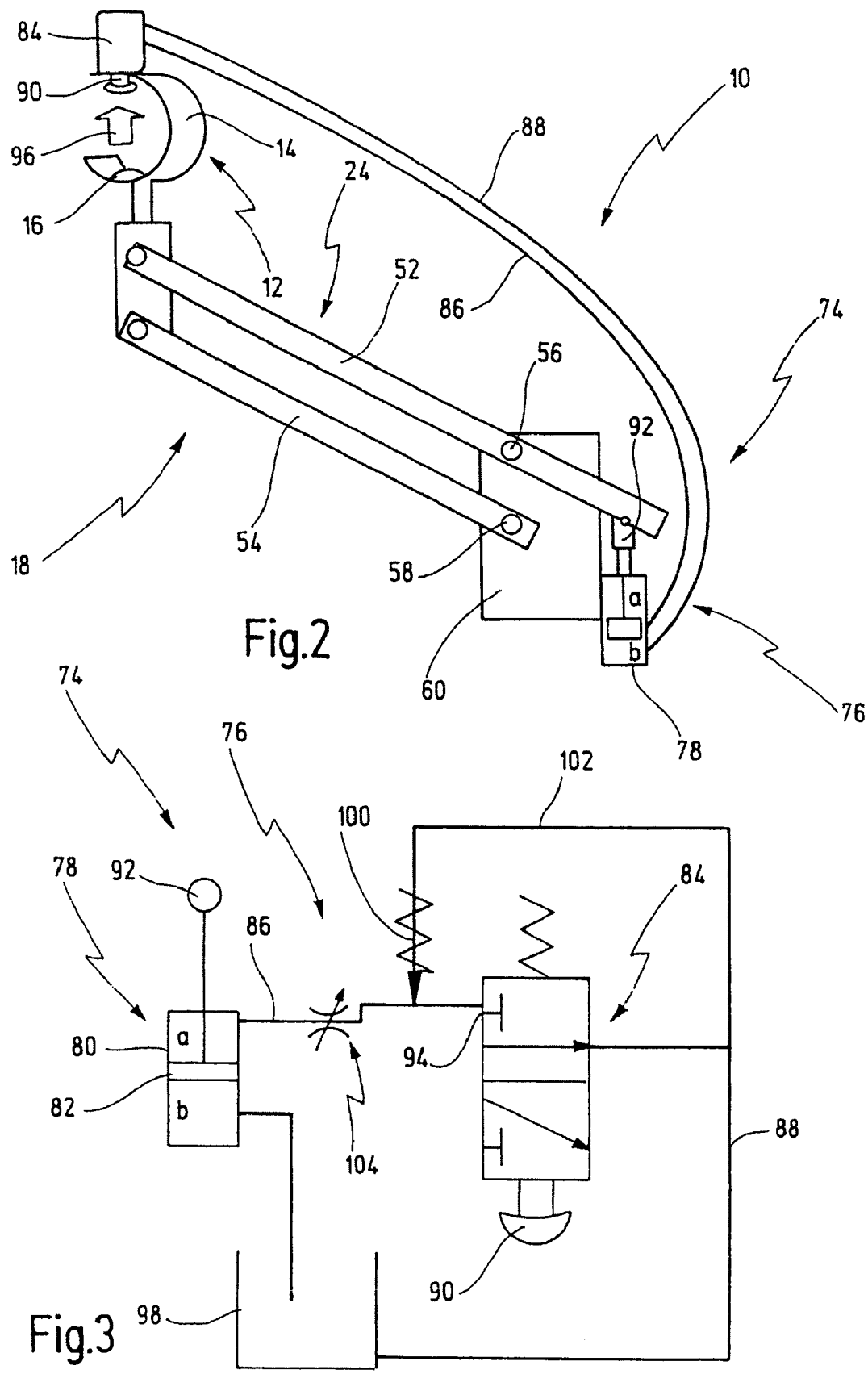
FIG. 2 shows a part of a device for supporting at least one arm in a partial view according to a first embodiment.
FIG. 3 shows a block diagram of the hydraulic circuit used in the control system according to FIG. 2.

With respect to FIG. 2 and FIG. 3, further details of the device 10 relating to a control system for adjusting the height of the supporting element 12 are described. FIG. 2 only shows a portion of the device 10 in the region of the supporting element 12 and the carrying arm 24.

The carrying structure 18 comprises a control system 74 which comprises a hydraulic circuit 76 for lowering or raising the at least one supporting element 12.

The hydraulic circuit 76 comprises a hydraulic ram 78. The hydraulic ram 78 comprises a cylinder 80 in which a piston 82 divides the interior of the cylinder 80 into a first chamber a and a second chamber b.

The hydraulic ram 78 is operatively connected to a control valve 84. The control valve 84 is connected to the chamber a of the ram 78 via a first hydraulic line 86, and the chamber b is connected to the control valve 84 via a second hydraulic line 88.

The control valve 84 is equipped with an operating element 90 which mechanically acts on the control valve 84.

The control valve 84 as well as the operating element 90 are arranged on the supporting element 12 in a position opposite to the contact pad 16, i.e. in the upper region of the supporting element 12. The operating element 90 extends into the C-shaped element 14 forming the supporting element 12.

Further, the parallelogram arm 52 of the carrying arm 24 is connected with a prolongation 92 of the piston 82 of the ram 78. The function of the hydraulic control system 74 is as follows:

When the operating element 90 is not actuated, the control valve 84 is closed. The operating element 90 or the control valve 84 itself is biased in the closed state of the control valve 84. In the closed state of the control valve 84, a port 94 of the control valve 84 is closed, thus preventing the hydraulic fluid which fills the chambers a and b of the ram 78, and the lines 86 and 88, is prevented from flowing. Thus, the supporting element 12 can neither be lowered nor raised in this case.

When the operating element 90, which is configured as a push button, is pressed, which is accomplished by simply raising the arm accommodated in the supporting element 12 according to an arrow 96, the control valve 84, i.e. the port 94 of the control valve 84 is opened so that the hydraulic fluid can flow from chamber a through the line 86, the control valve 84 and the line 88 into the chamber b or vice versa.

In the embodiment shown, when the supporting element 12 is lowered, carrying arm 24 moves downward, thus pulling the piston 82 in upward direction, thereby causing the hydraulic fluid from chamber a through the line 86 and a control valve 84 and the line 88 into the chamber b. For stopping the movement of the carrying arm 24, the operating person just has to release the operating element 90 which is simply achieved by leaning the arm on the contact pad 16 of the supporting element 12 again. Raising of the supporting element 12 is carried out in reversed manner, accordingly.

Further, a reservoir 98 for the hydraulic fluid is optionally provided in the hydraulic line 88. A pressure release valve 100 is positioned in the line 86 and, when opened, directly connects the line 86 to the reservoir 98, thereby allowing fluid to flow directly from the chamber a of the ram 78 into the reservoir 98 without passing through the control valve 84. This allows to release pressure in the circuit and to avoid overload situations of the hydraulic circuit 76.

Further, a restrictor 104 can be provided in the hydraulic circuit in order to adjust the flow resistance of the hydraulic medium flowing in the hydraulic circuit. The restrictor 104 could also be incorporated in the ram 78, or the restrictor 104 could be omitted in case that the inherent flow resistance of the hydraulic circuit is sufficient in order to limit the speed of the downward movement of the supporting element 12 when the control valve 84 is opened. The restrictor 104 advantageously acts as a damper which, in particular, damps the downward motion of the carrying arm 24.

What is claimed is:

1. A device for supporting at least one arm of an operating person during a surgical or medical operation, comprising:
    at least one supporting element for supporting said at least one arm of said operating person,
    a carrying structure for carrying said supporting element at which said supporting element is arranged,
    said carrying structure being configured such that said at least one supporting element can be lowered or raised for adjusting a height of said operating person's arm, and
    said carrying structure having a control system which comprises a hydraulic circuit for lowering or raising said at least one supporting element;
    wherein said hydraulic circuit comprises a hydraulic ram operatively connected to said supporting element and at least a control valve which can be closed and opened for controlling a flow of fluid between a first chamber and a second chamber of said hydraulic circuit; and
    wherein said control valve is operatively connected to an operating element for closing or opening said control valve, and wherein said operating element is arranged on said supporting element in a position above a portion of said supporting element on which said operating person's arm rests in use of said device.

2. The device of claim 1, wherein said supporting element can be lowered only when said control valve is open.

3. The device of claim 1, wherein said control valve is electrically actuable, and said operating element is an electrical switch.

4. The device of claim 1, wherein said control valve is mechanically actuable, and said operating element is a push button.

5. The device of claim 1, wherein at least one of said control valve and said operating element is biased such that said control valve is closed when said operating element is not actuated.

6. The device of claim 5, wherein a biasing load of said at least one of said control valve and said operating element is adjustable.

7. The device of claim 1, wherein a flow resistance of a hydraulic medium of said hydraulic circuit is adjustable.

* * * * *